(12) United States Patent
Hellou

(10) Patent No.: US 10,575,940 B2
(45) Date of Patent: Mar. 3, 2020

(54) INTRA-THORAX/ABDOMEN RESPIRATORY APPARATUS

(71) Applicant: Elias Hellou, Haifa (IL)

(72) Inventor: Elias Hellou, Haifa (IL)

(*) Notice: Subject to any disclaimer, the term of this patent is extended or adjusted under 35 U.S.C. 154(b) by 190 days.

(21) Appl. No.: 15/572,831

(22) PCT Filed: May 29, 2016

(86) PCT No.: PCT/IL2016/050553
§ 371 (c)(1),
(2) Date: Nov. 9, 2017

(87) PCT Pub. No.: WO2016/189539
PCT Pub. Date: Dec. 1, 2016

(65) Prior Publication Data
US 2018/0132994 A1    May 17, 2018

Related U.S. Application Data

(60) Provisional application No. 62/167,357, filed on May 28, 2015.

(51) Int. Cl.
*A61F 2/02* (2006.01)
*A61F 2/08* (2006.01)
*F03G 5/06* (2006.01)
*A61F 2/30* (2006.01)
*A61F 2/44* (2006.01)
*A61F 2/04* (2013.01)
(Continued)

(52) U.S. Cl.
CPC ............ *A61F 2/08* (2013.01); *A61F 2/30749* (2013.01); *A61F 2/4405* (2013.01); *F03G 5/06* (2013.01); *A61F 2002/043* (2013.01); *A61F 2002/0894* (2013.01); *A61F 2002/30668* (2013.01); *A61F 2002/482* (2013.01); *A61F 2220/0008* (2013.01); *F03G 7/06* (2013.01)

(58) Field of Classification Search
CPC ...... A61F 2/08; A61F 2002/0894; A61F 2/04; A61F 2002/043; A61F 2/02; A61H 31/00; A61H 31/02; A61H 1/00; A61H 2031/001; A61M 1/00; A61M 2210/1014; A61M 2210/1039; A61M 1/04; A61B 5/0809
See application file for complete search history.

(56) References Cited

U.S. PATENT DOCUMENTS

| 2,067,268 | A | 1/1937 | Hans |
| 2,652,047 | A | 9/1953 | Luck et al. |
| 6,814,076 | B2 | 11/2004 | Shusterman et al. |

(Continued)

FOREIGN PATENT DOCUMENTS

| FR | 2478996 | 3/1980 |
| WO | 2014011635 | 1/2014 |

OTHER PUBLICATIONS

International Search Report PCT/IL2016/050553 Completed Sep. 22, 2016; dated Sep. 25, 2016 5 pages.

(Continued)

*Primary Examiner* — Alvin J Stewart
(74) *Attorney, Agent, or Firm* — The Roy Gross Law Firm, LLC; Roy Gross

(57) ABSTRACT

An implantable respiratory apparatus including an expandable/contractible element; wherein at least part of the element is configured to be anchored to the subject's chest bones.

20 Claims, 5 Drawing Sheets

(51) Int. Cl.
*A61F 2/48* (2006.01)
*F03G 7/06* (2006.01)

(56) References Cited

U.S. PATENT DOCUMENTS

| | | | | |
|---|---|---|---|---|
| 8,281,792 B2* | 10/2012 | Royalty | ............... | A61B 5/0809 |
| | | | | 128/897 |
| 2006/0041183 A1* | 2/2006 | Massen | ................. | A61F 2/0036 |
| | | | | 600/16 |
| 2006/0184206 A1* | 8/2006 | Baker, III | ............ | A61N 1/3785 |
| | | | | 607/35 |
| 2006/0247729 A1* | 11/2006 | Tehrani | ................ | A61N 1/3601 |
| | | | | 607/42 |
| 2007/0250162 A1* | 10/2007 | Royalty | ............... | A61B 5/0809 |
| | | | | 623/3.11 |
| 2015/0190219 A1* | 7/2015 | Kothera | ................... | A61F 2/08 |
| | | | | 623/24 |
| 2018/0177584 A1* | 6/2018 | Saber | ........................ | A61F 2/08 |
| 2019/0254906 A1* | 8/2019 | Johnson | ................ | A61B 5/021 |

OTHER PUBLICATIONS

Written Opinion of the International Searching Authority PCT/IL2016/050553 dated Sep. 25, 2016 6 pages.

* cited by examiner

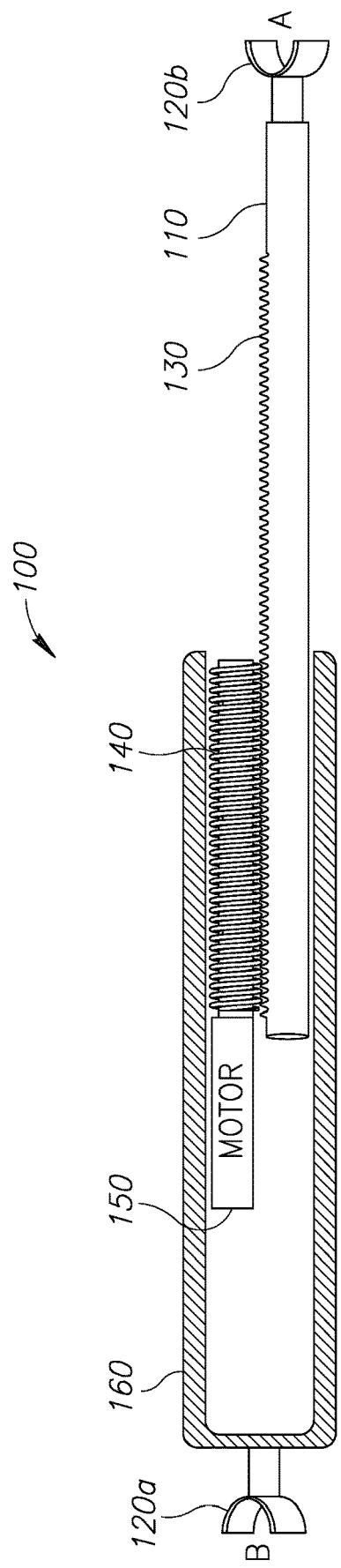
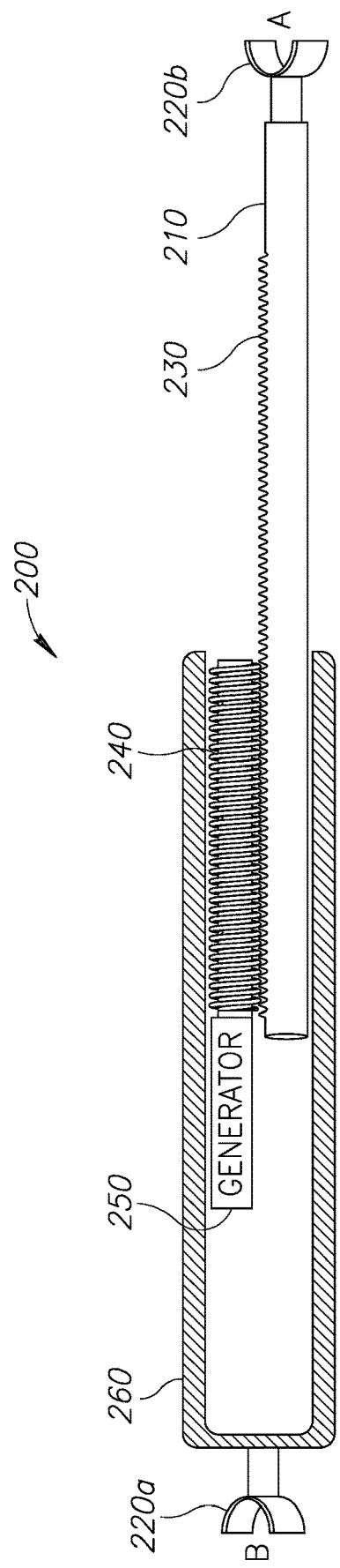
FIG.1
FIG.2

INTRA-THORAX/ABDOMEN RESPIRATORY APPARATUS

RELATED APPLICATIONS

This application is a National Phase of PCT Patent Application No. PCT/IL2016/050553 having International filing date of May 29, 2016, which claims the benefit of priority of U.S. Provisional Application No. 62/167,357 filed on May 28, 2015 entitled INTRA-THRAX/ABDOMEN RESPIRATORY APPARATUS. The contents of the above applications are all incorporated by reference as if fully set forth herein in their entirety.

TECHNICAL FIELD

The present disclosure generally relates to the field of apparatuses for intra-thorax/abdomen ventilation and/or power generation, and methods using same.

BACKGROUND

Respiratory disease is a medical term that encompasses pathological conditions affecting the organs and tissues that make gas exchange possible in higher organisms, and includes conditions of the upper respiratory tract, trachea, bronchi, bronchioles, alveoli, pleura and pleural cavity, and the nerves and muscles of breathing.

Mechanical ventilation is necessary when the patient's spontaneous ventilation is inadequate to maintain life. Common medical indications requiring mechanical ventilation: Acute lung injury (including ARDS, trauma), Apnea with respiratory arrest (including cases from intoxication), Acute severe asthma requiring intubation, Chronic obstructive pulmonary disease (COPD), Guillain-Barré syndrome, myasthenia gravis, spinal cord injury, or the effect of anesthetic and muscle relaxant drugs.

As of today, the majority of patients in need of mechanical ventilation devices are treated with non-implantable devices, which produce positive pressure to inflate the chest and expand it, similar to natural ventilation.

However, mechanical ventilators may have adverse effects and lead to medical problems such as pneumothorax, airway injury, alveolar damage, and ventilator-associated pneumonia. Other complications include diaphragm atrophy, decreased cardiac output, and oxygen toxicity. One of the primary complications that presents in patients mechanically ventilated is acute lung injury (ALI)/acute respiratory distress syndrome (ARDS). In fact, ALI/ARDS are recognized as significant contributors to patient morbidity and mortality.

There therefore remains a need for mechanical ventilators, which may assist subjects suffering from respiratory failure breathing while causing minimal complications.

Medical devices are often implanted into humans and animals as a means of achieving a desired result. Examples of these implanted medical devices include: pacemakers (i.e., a device used to stimulate or regulate contractions of the heart muscle); defibrillators (i.e., a device used to counteract fibrillation of the heart muscle and restore a normal heartbeat by applying a brief electric shock); bone growth stimulation devices, pain blocking/attenuation devices, brain implant devices, and cochlear implant devices. Typically, these devices are powered by an internal battery or external battery pack (i.e., a battery pack implanted within the patient but external to the medical device). Unfortunately, these batteries/battery packs have a finite life span and, after a period of time, must be replaced or recharged. There therefore remains a need for systems, which may obviate the need for battery replacement.

SUMMARY

The present disclosure relates to implantable (intra-thorax and/or intra-abdomen) apparatus and method for negative ventilation and/or power generation.

Positive pressure ventilators that force air into a patient's lungs are often used to aid breathing in patients with respiratory failure, but these devices often lead to ventilation associated medical problems, such as pneumothorax, airway injury, alveolar damage, ventilator-associated pneumonia and/or hemodynamic compromise.

Advantageously, the respiratory apparatus disclosed herein may be ventilation apparatus configured to provide negative pressure ventilation of the subject, i.e. utilizing the physiology of breathing. According to embodiments herein, the ventilation apparatus may include a motorized element configured to be anchored to the chest bones of a subject suffering from respiratory failure. Within the cavity, a motor may cause the element to expand and contract at a pace similar to normal breathing. When expanded, the rib cage, and thus the pleural cavity, is enlarged, thereby creating a negative pressure, which consequently causes air to be sucked into the lungs. Similarly, when the element is contracted, the rib cage is contracted, thereby creating a positive pressure pushing air out of the lungs.

Advantageously, the ventilator apparatus may be implanted into the subject (intra-thorax/abdomen), and may require no physical connection to external medical devices, such as, but not limited to, a ventilation machine. Thus, no or minimal disturbance and discomfort is caused to the patient, who may carry on with his or her normal activities.

As a further advantage, the ventilation apparatus may be programmable. For example, the respiratory apparatus may be programmed to provide ventilation at a different frequency when the subject is awake and when asleep. As another example, the apparatus may be programmed to provide a weaning protocol, gradually reducing the patient's need for mechanical ventilation.

In addition, the ventilation apparatus may be adjustable based on the patient's immediate needs. For example, the apparatus may, upon receiving an indication from the patient or from a sensor, change the operation mode of the apparatus, for instance in order to allow the patient to cough or talk. As another example, the apparatus may adjust its operation mode based on feed-back received from the patient and/or a sensor, thereby allowing the ventilation provided to be responsive to the respiratory needs of the patient.

According to other embodiments, the respiratory apparatus disclosed herein may be capable of serving as a generator assembly converting mechanical motion (respiration) into electrical energy. According to this embodiment, the respiratory apparatus may function as a generator and include an expandable/contractible element configured to be anchored to the chest bones of a subject implanted or intended for implantation with a medical device (i.e. a pacemaker). Within the cavity, the expandable/contractible element may expand and contract along with the patient's breathing. That is, during inhalation, when the pleural cavity is enlarged, the element may be (automatically) released into its expanded configuration, whereas during exhalation, when the pleural cavity is contracted, the element is forced into its contracted configuration. The motion of the element caused by the subject's breathing may be converted into electrical power, serving as a power source for the implanted medical device and/or capable of recharging the battery of the implanted medical device, thereby obviating the need for batteries or other finite power sources requiring replacement.

According to some embodiments, there is provided an intra-thorax/abdomen respiratory apparatus including an expandable/contractible element; wherein at least part of the expandable/contractible element is configured to be anchored, posteriorly and anteriorly, to the subject's chest bones. According to some embodiments, the subject may suffer from respiratory failure. According to some embodiments, the implantable respiratory apparatus may be a ventilator.

According to some embodiments, the intra-thorax/abdomen respiratory apparatus may further include a motor configured to activate the expandable/contractible element, thereby causing inhalation and exhalation of air.

According to some embodiments, the intra-thorax/abdomen respiratory apparatus may further include an attachment mechanism configured to anchor the implantable respiratory apparatus, posteriorly and anteriorly, to the subject's chest bones.

According to some embodiments, the intra-thorax/abdomen respiratory apparatus may further include a power source. According to some embodiments, the power source may be wirelessly chargeable.

According to some embodiments, the expandable/contractible element may include a rod. According to some embodiments, the expandable/contractible element may include a material configured to change its configuration in response to an electrical, magnetic and/or mechanical stimulus. According to some embodiments, the intra-thorax/abdomen respiratory apparatus may further include a mechanism mechanically coupled to the expandable/contractible element. According to some embodiments, a mechanism may be configured to cause the expansion or the contraction of the expandable/contractible element. According to some embodiments, the mechanism may be activated by the motor.

According to some embodiments, the intra-thorax/abdomen respiratory apparatus may further include a processor, the processor configured to control an operation mode of the intra-thorax/abdomen respiratory apparatus. According to some embodiments, the operation mode may be selected from sleep mode, awake mode, active mode, talk mode, cough mode, weaning mode or any combination thereof. Each possibility is a separate embodiment.

According to some embodiments, the processor may be configured to wirelessly receive signals indicative of the subject's respiratory needs from a communication module. According to some embodiments, the communication module is user activated.

According to some embodiments, the processor may be functionally connected to a sensor. According to some embodiments, the sensor may be selected from a pH sensor, a CO2 sensor, a capnograph, a PPG sensor or any combination thereof. Each possibility is a separate embodiment.

According to some embodiments, there is provided an intra-thorax/abdomen respiratory apparatus including an expandable/contractible element; wherein at least part of the expandable/contractible element is configured to be anchored, posteriorly and anteriorly, to the subject's chest bones. According to some embodiments, the subject is an autonomously breathing subject. According to some embodiments, the subject's breathing may cause expansion and contraction of the expandable/contractible element.

According to some embodiments, the expansion and/or contraction of the expandable/contractible element may generate electrical power. According to some embodiments, the electrical power generated may serve as a power source to an implanted medical device. According to some embodiments, the implanted medical device may include a pacemaker.

According to some embodiments, the intra-thorax/abdomen respiratory apparatus may further include a mechanism mechanically coupled to the expandable/contractible element. According to some embodiments, expansion and/or contraction of the expandable/contractible element may activate the mechanism. According to some embodiments, activation of the mechanism may generate electrical power. According to some embodiments, the expandable/contractible element may include a rod.

According to some embodiments, the intra-thorax/abdomen respiratory apparatus may further include an attachment mechanism configured to anchor the apparatus, posteriorly and anteriorly, to the subject's chest bones.

According to some embodiments, there is provided a method for providing ventilation to a subject suffering from respiratory failure, the method including: implanting a ventilator within the thorax/abdomen of the subject, such that an expandable/contractible element of the ventilator is attached to the subject's chest bone anteriorly and posteriorly; activating a mechanism causing repeated expansion and contraction of the expandable/contractible element, thereby inducing expansion and contraction of the subject's pleural cavity, so as to affect inhalation and exhalation of the subject, respectively.

According to some embodiments, there is provided a method for providing electrical energy to an implanted medical device, the method including: implanting a generator within a thorax/abdomen of a subject implanted with a medical device such that an expandable/contractible element of the generator is attached to the subject's chest bone anteriorly and posteriorly; and such that the subject's inhalation and/or exhalation causes expansion and contraction of the expandable/contractible element, respectively; utilizing a mechanism configured to generate electrical power from the expansion and/or contraction of the expandable/contractible element; transferring the generated electrical power to the implanted medical device. According to some embodiments, the medical device may be a pacemaker.

Certain embodiments of the present disclosure may include some, all, or none of the above advantages. One or more technical advantages may be readily apparent to those skilled in the art from the figures, descriptions and claims included herein. Moreover, while specific advantages have been enumerated above, various embodiments may include all, some or none of the enumerated advantages.

BRIEF DESCRIPTION OF THE DRAWINGS

Examples illustrative of embodiments are described below with reference to figures attached hereto. In the figures, identical structures, elements or parts that appear in more than one figure are generally labeled with a same numeral in all the figures in which they appear. Alternatively, elements or parts that appear in more than one figure may be labeled with different numerals in the different figures in which they appear. Dimensions of components and features shown in the figures are generally chosen for convenience and clarity of presentation and are not necessarily shown in scale. The figures are listed below.

FIG. 1 schematically illustrates an intra-thorax/abdomen ventilation apparatus, according to some embodiments;

FIG. 2 schematically illustrates an intra-thorax/abdomen generator, according to some embodiments;

DETAILED DESCRIPTION

Figure 3A:
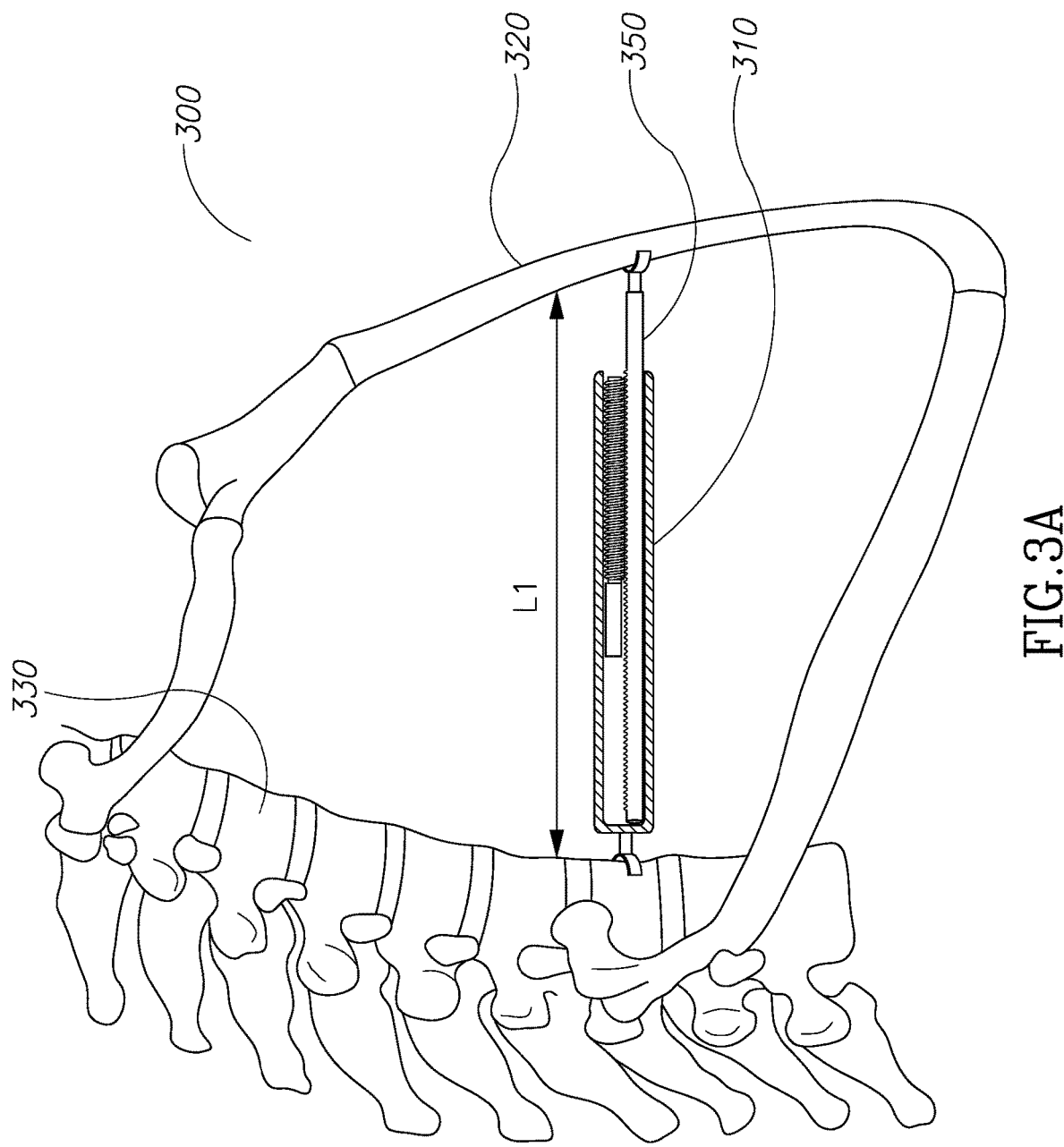
FIG. 3A-3C schematically illustrate an intra-thorax/abdomen respiratory device anchored to a rib cage, according to some embodiments.

In the following description, various aspects of the disclosure will be described. For the purpose of explanation, specific configurations and details are set forth in order to provide a thorough understanding of the different aspects of the disclosure. However, it will also be apparent to one skilled in the art that the disclosure may be practiced without specific details being presented herein. Furthermore, well-known features may be omitted or simplified in order not to obscure the disclosure.

There is provided, according to some embodiments, an intra-thorax/abdomen apparatus comprising an element configured to be expanded and contracted.

According to some embodiments, as used herein, the term "intra-thorax/abdomen respiratory apparatus" may refer to an apparatus configured to be attached to, anchored to or otherwise associated within the thoracic and/or abdominal cavity of the subject, anteriorly and posteriorly. According to some embodiments, the apparatus may be attached to, anchored to or otherwise associated with the subject's chest bones. As used herein, the term "chest bones" may refer to the subject's ribs, sternum, vertebra or other suitable attachment points within the thorax/abdomen of the subject. The apparatus is further configured to influence or be influenced by the subject's respiration.

According to some embodiments, the apparatus includes an expandable/contractible element configured to change, actively or passively, its configuration. According to some embodiments, the apparatus may further include a housing configured to at least partially receive the expandable/contractible element.

According to some embodiments, the expandable/contractible element may be a rod. As used herein, the term "rod" may refer to any elongated member configured to be directly or indirectly connected to subject's rib cage, anteriorly and posteriorly. According to some embodiments, the apparatus may include more than one rod, such as 2, 3, 4, 5 or more rods. Each possibility is a separate embodiment. According to some embodiments, the rod may be configured to be expanded/contracted along its longitudinal axis. Additionally or alternatively, the rod may be moved relative to its housing so as to protrude further in or out therefrom. It is understood that other configurations of the rod configured to enlarge the rib cage along an anterior/posterior axis and thus cause a negative pressure therewithin may further be applicable and, as such, fall within the scope of this disclosure.

According to some embodiments, the expandable/contractible element may be a material configured to change its configuration in response to an electrical, magnetic or mechanical stimulus.

According to some embodiments, the apparatus may be configured to be attached to, anchored to or otherwise associated with the sternum on the one end thereof and to a rib bone (posteriorly) at the other end thereof. According to some embodiments, the apparatus may be configured to be attached to, anchored to or otherwise associated with the sternum on the one end thereof and to the vertebra and/or vertebral column at the other end thereof. According to some embodiments, the apparatus may be configured to be attached to, anchored to or otherwise associated with a rib bone (anteriorly—e.g. in proximity to the sternum) on the one end thereof and to the vertebra and/or vertebral column at the other end thereof. According to some embodiments, the apparatus may be configured to be attached to, anchored to or otherwise associated with a rib bone (anteriorly—e.g. in proximity to the sternum) on the one end thereof and to a rib bone (posteriorly—e.g. in proximity to the vertebral column) at the other end thereof. According to some embodiments, the anterior and posterior attachment may be to a same rib bone. According to some embodiments, the anterior and posterior attachment may be to a different rib bone.

According to some embodiments, posterior and/or anterior attachment to a rib bone may be at both sides of the rib cage. According to some embodiments, the apparatus may be anchored to more than one rib bone, such as 2, 3, 4 or more ribs. Each possibility is a separate embodiment. According to some embodiments, the attachment may be made using any traditional surgical fastener, such as, but not limited to, surgical adhesives, staples, screws or any other suitable mechanism for fastening the apparatus. As a non-limiting example, the apparatus may be screwed into the rib and/or sternum. As another non-limiting example, the apparatus may include a hook and lock mechanism configured to embrace the rib and/or sternum and thereby fasten the apparatus thereto.

According to some alternative embodiments, the intra-thorax/abdomen apparatus may be configured to be positioned within an abdominal cavity (intra peritoneal). According to some embodiments, the intra-thorax/abdomen apparatus may be configured to be positioned within a pleural cavity (intra-pleural). According to some embodiments, the intra-thorax/abdomen apparatus may be configured to be positioned above the diaphragm of the subject. According to some embodiments, the intra-thorax/abdomen apparatus may be configured to be positioned below the diaphragm of the subject. According to some embodiments, the intra-thorax/abdomen apparatus may be configured to be attached to the diaphragm of the subject.

According to some embodiments, as used herein, the term "implanted" may refer to an apparatus which is positioned within the patient, when in use. The power source supplying power to the apparatus (e.g. a long-term battery) may likewise be implanted, for example, under the skin of the subject. According to some embodiments, the power source may be co-implanted with a wireless charging apparatus. According to some embodiments, the power source may include a wire pierced through the subject's skin, configured to rely on an external power supply. According to some embodiments, the wire may be tunneled under the subject's skin, thereby avoiding or significantly reducing infections and/or inflammation of sensitive tissue.

According to some embodiments, as used herein, the term "intra-thorax/abdomen" may refer to an apparatus located within a subject's upper body. According to some embodiments, as used herein, the term "intra-thorax/abdomen" may refer to "inside the thorax", below, above or partially below and partially above the diaphragm.

As used herein, the terms "patient" and "subject" may interchangeably be used and may relate to a subject being implanted with or suitable for implantation with the intra-thorax/abdomen respiratory apparatus disclosed herein.

According to some embodiments, the subject may suffer from respiratory failure. According to some embodiments, the subject may suffer from acute lung injury (including ARDS, trauma), apnea with respiratory arrest (including cases from intoxication), acute severe asthma, chronic obstructive pulmonary disease (COPD), Guillain-Barré syndrome, myasthenia gravis, spinal cord injury, effect of anesthetic and muscle relaxant drugs or any combination thereof. According to some embodiments, the subject may suffer from a chronic condition such as, but not limited to, amyotrophic lateral sclerosis (ALS), spinal muscular atrophy (SMA), Duchenne muscular dystrophy, or any other disease or condition. Each possibility is a separate embodiment.

According to some (alternative) embodiments, the subject may be an autonomously breathing subject, such as, but not limited to, a normally breathing subject. According to some embodiments, the subject may be implanted with or designated for implantation with a medical device, such as, but not limited to, a pacemaker.

According to some embodiments, the intra-thorax/abdomen respiratory apparatus may be an implantable ventilator configured to provide for and/or assist a subject's breathing. According to some embodiments, the intra-thorax/abdomen respiratory apparatus may serve as a generator assembly configured to generate electrical power from the mechanical motion caused during breathing.

According to some embodiments, the intra-thorax/abdomen respiratory apparatus may include a motor (electrical and/or magnetic, such as a linear motor or a step motor) configured to activate a mechanism configured to control the expansion and contraction of the expandable/contractible element. According to some embodiments, the mechanism may include a cogwheel, wherein rotation of the cogwheel causes the expansion or the contraction of the expandable/contractible element. According to some embodiments, the mechanism may include a pinion gear mechanically coupled to the housing and configured to mesh with a rack gear on the expandable/contractible element, such that rotational movement of the pinion gear is converted into a movement of the expandable/contractible element relative to the housing. According to some embodiments, the mechanism configured to control the expansion and contraction of the expandable/contractible element may include a linear induction motor. According to some embodiments, the mechanism may include an electrical, magnetic and/or mechanical signal configured to induce a configuration change in a material having inducible configuration change properties, such as, but not limited, to a balloon. However, any other mechanism configured to cause expansion/contraction of the rib cage is also applicable and, as such, falls within the scope of this disclosure.

According to some embodiments, expansion of the expandable/contractible element causes the element to exert a pressure on the chest bones to which it is attached (anteriorly and posteriorly) and thereby to cause expansion of the rib cage. As a result, a negative pressure is created within the pleural cavity leading air to be sucked into the lungs, in a manner similar to normal inhalation. According to some embodiments, contraction of the expandable/contractible element releases the pressure on the chest bones and may thus lead to a contraction of the pleural cavity. As a result, a positive pressure is created within the pleural cavity leading air to be pushed out of the lung in a manner similar to normal exhalation.

According to some embodiments, the intra-thorax/abdomen respiratory apparatus may include or be functionally connected to a processor configured to control the operation of the intra-thorax/abdomen respiratory apparatus. According to some embodiments, operation of the intra-thorax/abdomen respiratory apparatus may be pre-programmed According to some embodiments, the processor may include a plurality of pre-programmed operation modes. Non-limiting examples of suitable pre-programmed operation modes include: sleep mode, awake mode, active mode, talk mode, cough mode, weaning mode or any other suitable mode, which may influence the operation of the intra-thorax/abdomen respiratory apparatus. Each possibility is a separate embodiment. For example, the cough mode may include a mode wherein the expandable/contractible element is initially expanded to cause the intra-pleural cavity to be filled with air (while keeping the vocal cords closed) followed by a rapid contraction of the expandable/contractible element (simultaneous with an opening of the vocal cords). As another non-limiting example, the apparatus may be programmed to provide a weaning protocol gradually reducing the patient's need for mechanical ventilation. As another non-limiting example, the apparatus may operate at a slower respiration rate during sleep mode than during awake mode.

According to some embodiments, the implantable respiratory apparatus may include communication means configured to receive and/or provide instructions with regards to the operation of the implantable respiratory apparatus. As a non-limiting example, the communication means may be a user interface, such as: switches, a keyboard, a remote control, a mobile phone application or any other suitable means configured to allow a user or a healthcare provider to control the operation of the implantable respiratory apparatus. According to some embodiments, the communications means may be configured to receive instructions as to the respiratory needs of the patient. According to some embodiments, the communication means may be configured to receive instructions from a user, from a sensor or from any other suitable device configured to provide an indication of the respiratory needs of a patient.

According to some embodiments, the communication means may be configured to communicate a signal indicative of the respiratory needs of the subject to the processor. According to some embodiments, the communication means may be configured to wirelessly communicate signals indicative of the respiratory needs of the subject to the processor, for example, through Bluetooth or similar technologies of wireless information transfer. According to some embodiments, the intra-thorax/abdomen respiratory apparatus may be configured to provide instructions, such as, but not limited to, vocal instructions to the user. For example, the intra-thorax/abdomen respiratory apparatus may be configured to provide instructions to the user as to when to open or close his/her vocal cords.

According to some embodiments, the intra-thorax/abdomen respiratory apparatus may include at least one sensor. Additionally or alternatively, the intra-thorax/abdomen respiratory apparatus may be functionally coupled to at least one sensor. As used herein, the term at least one with regards to sensors may include 1, 2, 3, 4, 5 or more sensors. Each possibility is a separate embodiment. According to some embodiments, the intra-thorax/abdomen respiratory apparatus may be configured to operate in a closed feed-back loop with the at least sensor. That is, the operation of the intra-thorax/abdomen respiratory apparatus may be automatically adjusted based on inputs received from the sensor. Non-limiting examples of suitable sensors include a pH sensor, a $CO_2$ sensor, a capnograph, a PPG sensor or any combination thereof. According to some embodiments, the sensor may provide a signal indicative of the efficiency of ventilation. For example, by being functionally connected to a pH sensor, the intra-thorax/abdomen respiratory apparatus may identify acidification/alkalization of the patient's blood and, in response thereto, increase/reduce the ventilation of the patient. This may be of particular importance when weaning the patient from mechanical ventilation.

According to some embodiments, the intra-thorax/abdomen respiratory apparatus may be used together with commonly used devices configured to keep the airways open, such as, but not limited to, an intubation tube, an endotracheal tube, a tracheostomy tube, a nasopharyngeal airway tube, any other tube or device configured to generate/maintain an open airway or combinations thereof. Each possibility is a separate embodiment.

According to some embodiments, the intra-thorax/abdomen respiratory apparatus may include a mechanism configured to generate electrical power from respiratory motion. According to some embodiments, the apparatus may further include an energy storage device (e.g., a battery or a capacitor) configured to store the electrical energy. According to some embodiments, the mechanism may include a cogwheel, wherein respiratory motion, i.e. the expansion and contraction of the rib cage, causes rotation of the cogwheel. According to some embodiments, the mechanism may include a pinion gear configured to mesh with a rack gear on the expandable/contractible element, such that movement of the element causes rotational movement of the pinion gear, which may be converted into electrical power. According to some embodiments, exhalation, causing contraction of the rib cage and the pleural cavity, may generate a push on the expandable/contractible element, leading to rotational movement of the pinion gear on the rack gear. According to some embodiments, inhalation, affecting expansion of the rib cage and the pleural cavity, may cause a pull on the element, which subsequently causes an opposite rotational movement of the pinion gear on the rack gear.

According to some embodiments, the implanted medical device may include a pacemaker, a defibrillator (i.e., a device used to counteract fibrillation of the heart muscle and restore a normal heartbeat by applying a brief electric shock); bone growth stimulation devices, pain blocking/attenuation devices, brain implant devices, cochlear implant devices, telemedicine monitoring devices, glucose sensors, artificial pancreas, retinal implants or any combination thereof. Each possibility is a separate embodiment.

Reference is now made to FIG. 1, which schematically illustrates an intra-thorax/abdomen ventilator 100, according to some embodiments. Intra-thorax/abdomen ventilator 100 includes attachment elements 120a and 120b configured to connect intra-thorax/abdomen ventilator 100 to the chest bones (not shown) anteriorly and posteriorly, of a subject suffering from respiration failure. Intra-thorax/abdomen ventilator 100 further includes a housing 160 having incorporated therein (or otherwise associated therewith) a motorized rod 110. Motorized rod 110 includes a rack gear 130 configured to mesh with a pinion gear 140, mechanically associated with housing 160. A rotational movement of pinion gear 140 on rack gear 130 is actuated by motor 150 and is configured to bring about expansion of motorized rod 110 by causing its outward movement relative to housing 160 or to bring about contraction of rod 110 by causing an inward movement relative to housing 160. Motor 150 is configured to actuate expansion or contraction of motorized rod 110 at a pace similar to normal exhalation/inhalation cycles, by changing the direction of the rotational movement of pinion gear 140 on rack gear 130. Thus, due to the firm attachment of intra-thorax/abdomen ventilator 100 to the chest bones of the subject, through attachment elements 120a and 120b, the repeated expansion and contraction of motorized rod 110 results in the expansion/contraction of the rib cage, thereby causing air to be sucked in or pushed out of the lungs in a manner mimicking normal respiration, as essentially described herein.

Reference is now made to FIG. 2, which schematically illustrates an intra-thorax/abdomen generator 200, according to some embodiments. Intra-thorax/abdomen generator 200 includes attachment elements 220a and 220b, configured to connect intra-thorax/abdomen generator 200 to the chest bones (not shown) anteriorly and posteriorly of an autonomously breathing subject. Intra-thorax/abdomen generator 200 further includes a housing 260 having incorporated therein (or otherwise associated therewith) a rod 210. Rod 210 includes a rack gear 230 configured to mesh with a pinion gear 240, mechanically associated with housing 260. Due to the firm attachment of intra-thorax/abdomen generator 200 to the chest bones of the subject, through attachment elements 220a and 220b, the subject's breathing, causing expansion and contraction of the rib cage (not shown), induces an expansion/contraction of rod 210. That is, during inhalation, rod 110 is expanded, causing rotational movement of pinion gear 240 on rack gear 230, which may be converted into electrical power. Similarly, during exhalation, rod 110 is contracted, thereby once again inducing rotational movement of pinion gear 240 on rack gear 230, which may be transformed into electrical power. The electrical power generated may be stored by generator 250 and/or transformed from generator 250 to a medical device, such as a pacemaker (not shown).

Reference is now made to FIG. 3A, which schematically illustrates a section of a rib cage 300 having an intra-thorax/abdomen respiratory apparatus 310 attached anteriorly to sternum 320 at a one end thereof and posteriorly to vertebral column 330 at the other end thereof (for simplicity only a single rib has been drawn). Rib cage 300 may have a contracted configuration A in which the distance between sternum 320 and vertebral column 330 is L1. In contracted configuration A, a rod 350 of intra-thorax/abdomen respiratory apparatus 310 is in a contracted configuration, either as a result of the operation of intra-thorax/abdomen respiratory apparatus 310 (when intra-thorax/abdomen respiratory apparatus 310 is a ventilator) or as a result of exhalation (when intra-thorax/abdomen respiratory apparatus 310 is a generator).

Figure 3B:
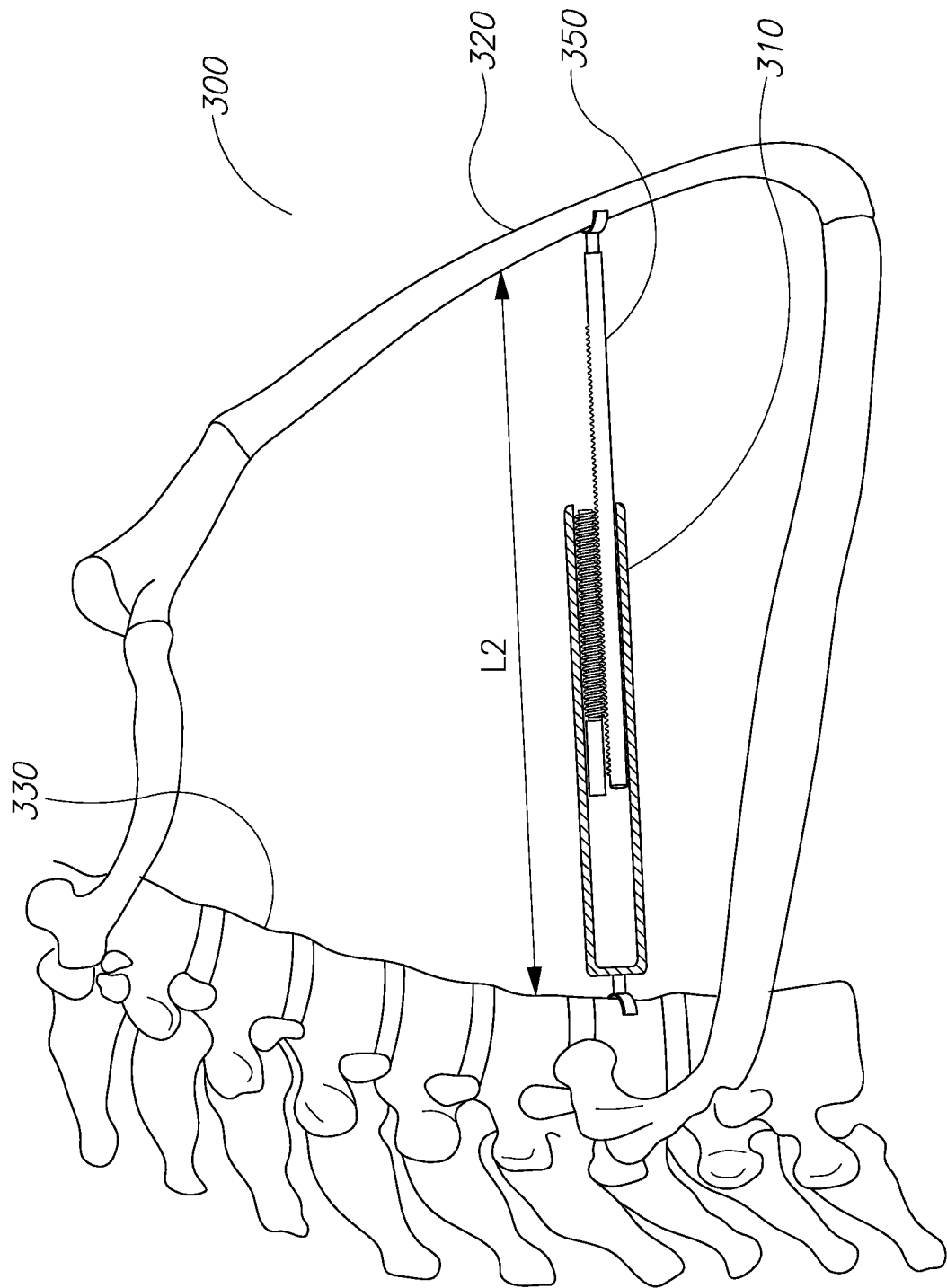

Reference is now made to FIG. 3B, which schematically illustrates a section of rib cage 300 in a mildly expanded configuration B in which the distance between sternum 320 and vertebral column 330 is L2 (L2>L1). In expanded configuration B, rod 350 of intra-thorax/abdomen respiratory apparatus 310 is in a moderately expanded configuration, either as a result of the operation of intra-thorax/abdomen respiratory apparatus 310 (when intra-thorax/abdomen respiratory apparatus 310 is a ventilator) or as a result of exhalation (when intra-thorax/abdomen respiratory apparatus 310 is a generator).

Figure 3C:
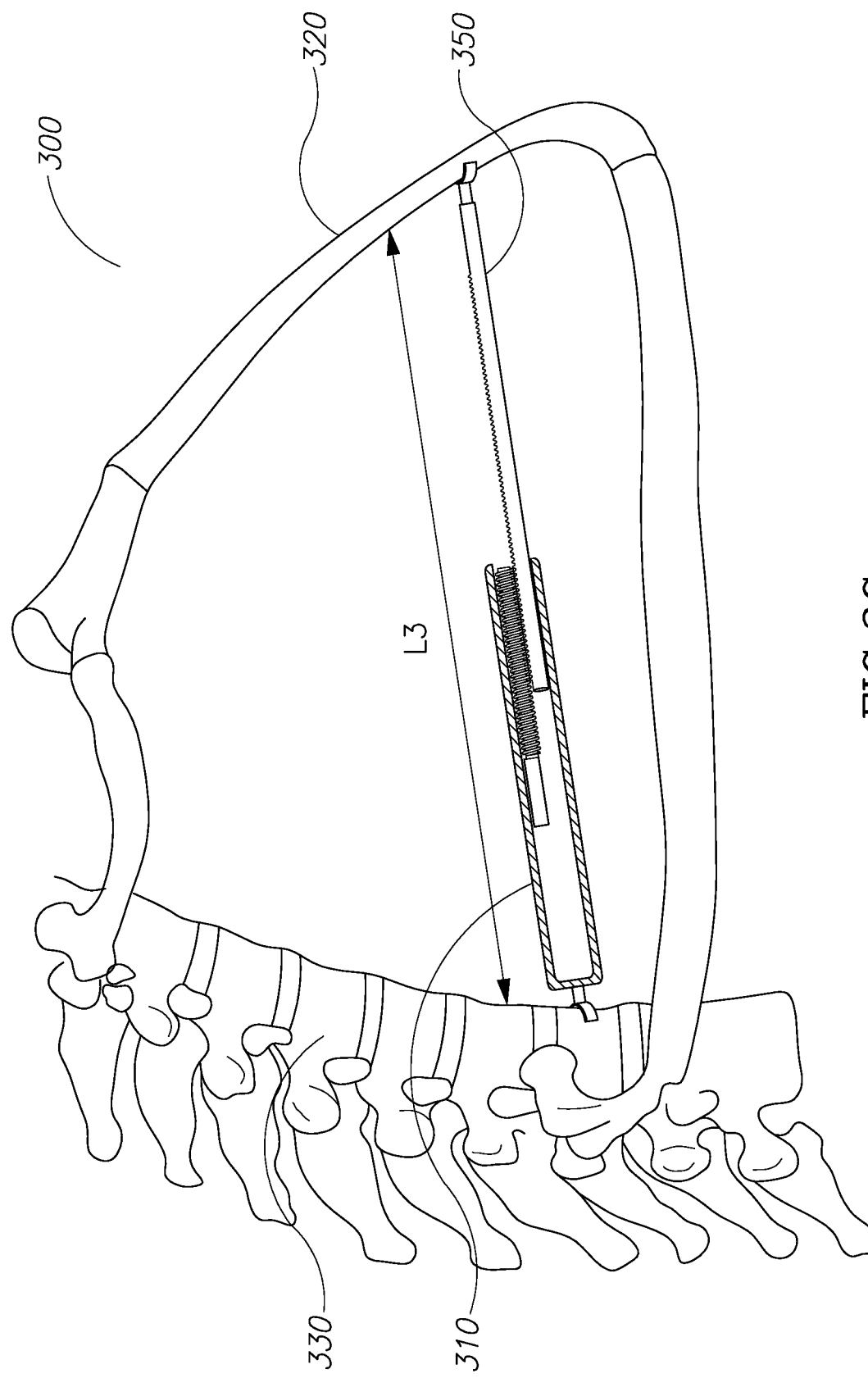

Reference is now made to FIG. 3C, which schematically illustrates a section of rib cage 300 in an essentially fully expanded configuration C in which the distance between sternum 320 and vertebral column 330 is L3 (L3>L2>L1). In expanded configuration C, rod 350 of intra-thorax/abdomen respiratory apparatus 310 is in a fully expanded configuration, either as a result of the operation of intra-thorax/abdomen respiratory apparatus 310 (when intra-thorax/abdomen respiratory apparatus 310 is a ventilator) or as a result of exhalation (when intra-thorax/abdomen respiratory apparatus 310 is a generator).

Figure 4A:
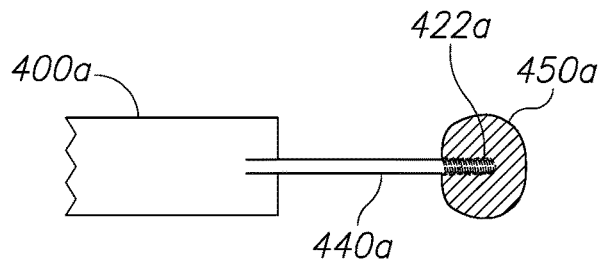
FIG. 4A-4E schematically illustrate attachment mechanisms of an intra-thorax/abdomen respiratory device anchored to a rib cage, according to some embodiments.

Reference is now made to FIG. 4A, which schematically illustrates attachment of an intra-thorax/abdomen respiratory device 400a to a rib/sternum 450a, according to some embodiments. Intra-thorax/abdomen respiratory device 400a includes a rod 440a configured to be expanded either as a result of the operation of intra-thorax/abdomen respiratory apparatus 400a (when operative as a ventilator) or as a result of exhalation (when operative as a generator). Rod 440a includes at a distal end thereof a screw 422a, which may be an integral part of rod 440a, molded on or otherwise attached to rod 440a. During implantation, screw 422a is screwed into rib/sternum 450a thereby securing rod 440a to rib/sternum 450a. It is understood that intra-thorax/abdomen respiratory device 400a is likewise attached posteriorly to the ribs, vertebra or vertebral column (not shown), utilizing a same or a different attachment mechanism.

Figure 4B:
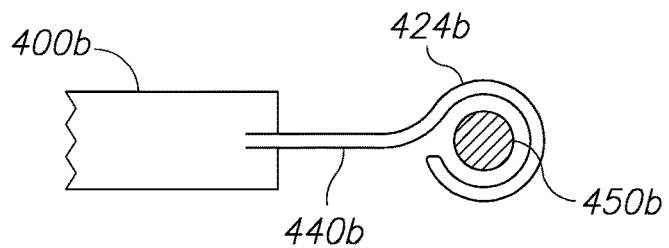

Reference is now made to FIG. 4B, which schematically illustrates attachment of an intra-thorax/abdomen respiratory device 400b to a rib/sternum 450b, according to some embodiments. Intra-thorax/abdomen respiratory device 400b includes a rod 440b configured to be expanded either as a result of the operation of intra-thorax/abdomen respiratory apparatus 400b (when operative as a ventilator) or as a result of exhalation (when operative as a generator). Rod 440b includes, at a distal end thereof, a hook 424b, which may be an integral part of rod 440b, molded on or otherwise attached to rod 440b. During implantation, hook 424b is hooked onto rib/sternum 450b such that rod 440b is secured to rib/sternum 450b by embracement of hook 424b around rib/sternum 450b. Hook 424b may be made of a material having a plasticity enabling it to be pulled open to an extent, which enables hook 424b to lock around rib/sternum 450b during attachment. Additionally or alternatively, hook 424b may include a hinge (not shown) configured to open hook 424b during attachment. It is understood that intra-thorax/abdomen respiratory device 400b is likewise attached posteriorly to the ribs, vertebra or vertebral column (not shown), utilizing a same or a different attachment mechanism.

Figure 4C:
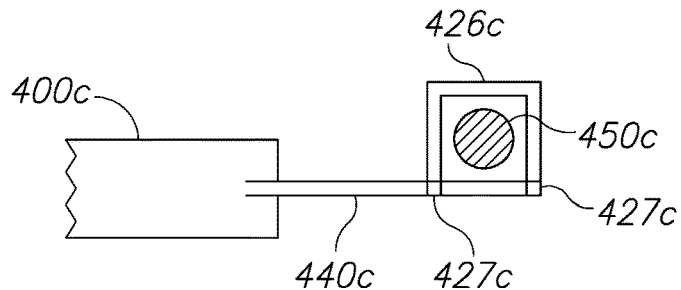

Reference is now made to FIG. 4C, which schematically illustrates attachment of an intra-thorax/abdomen respiratory device 400c to a rib/sternum 450c, according to some embodiments. Intra-thorax/abdomen respiratory device 400c includes a rod 440c configured to be expanded either as a result of the operation of intra-thorax/abdomen respiratory apparatus 400c (when operative as a ventilator) or as a result of exhalation (when operative as a generator). Rod 440c includes, at a distal end thereof, a cage 426c, here illustrated having a rectangular shape, however any other suitable shape fitting the anatomy of the ribs/sternum is likewise applicable and thus within the scope of this disclosure. Cage 426c may be an integral part of rod 440c, molded on or otherwise attached to rod 440c. Once implanted, cage 426b encages rib/sternum 450c thereby fastening rod 440c to rib/sternum 450c. Prior to implantation, cage 426c is open, enabling cage 426c to fold around and thus encage rib/sternum 450c. Once correctly positioned, cage 426c may be locked utilizing locking mechanism 427c, such as, but not limited to, snap lockers and the like. It is understood that intra-thorax/abdomen respiratory device 400c is likewise attached posteriorly to the ribs, vertebra or vertebral column (not shown), utilizing a same or a different attachment mechanism.

Figure 4D:
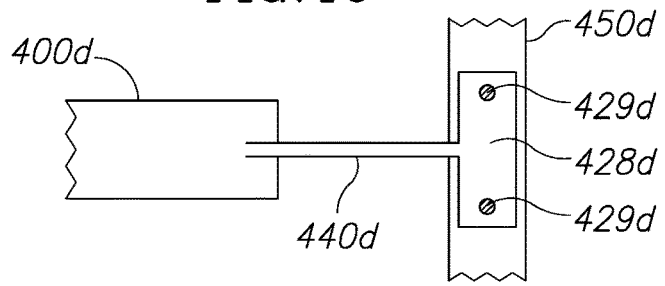

Reference is now made to FIG. 4D, which schematically illustrates attachment of an intra-thorax/abdomen respiratory device 400d to a rib/sternum 450d, according to some embodiments. Intra-thorax/abdomen respiratory device 400d includes a rod 440d configured to be expanded either as a result of the operation of intra-thorax/abdomen respiratory apparatus 400d (when operative as a ventilator) or as a result of exhalation (when operative as a generator). Rod 440d includes, at a distal end thereof, a mounting plate 428d, which may be an integral part of rod 440d, molded on or otherwise attached to rod 440d. During implantation, mounting plate 428d may be screwed into rib/sternum 450d, along a longitudinal axis thereof) using screws 429c. Additionally or alternatively, mounting plate 428c may be glued to rib/sternum 450d using suitable glues and/or adhesive tapes. It is understood that intra-thorax/abdomen respiratory device 400d is likewise attached posteriorly to the ribs, vertebra or vertebral column (not shown), utilizing a same or a different attachment mechanism.

Figure 4E:
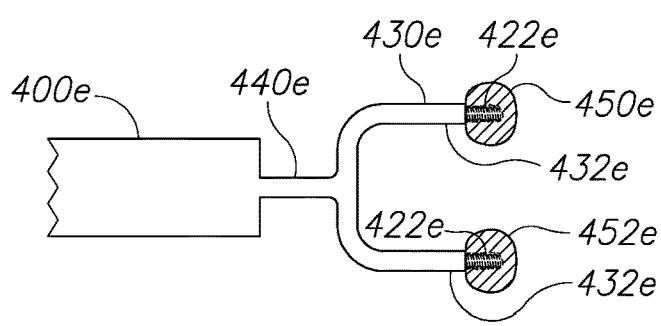

Reference is now made to FIG. 4E, which schematically illustrates attachment of an intra-thorax/abdomen respiratory device 400e to rib 450e and 452e, or to the sternum at positions 450e and 452e thereof; according to some embodiments. Intra-thorax/abdomen respiratory device 400e includes a rod 440e configured to be expanded either as a result of the operation of intra-thorax/abdomen respiratory apparatus 400e (when operative as a ventilator) or as a result of exhalation (when operative as a generator). Rod 440e includes, at a distal end thereof, into a bifurcation, here illustrated as a fork 430e, here illustrated as two fork prongs, however additional fork prongs are also applicable and within the scope of this disclosure. Fork 430e may be an integral part of rod 440e (e.g. rod 440e may split into fork 430e), molded on or otherwise attached to rod 440e. Fork 430e includes, at a distal end of fork prong 432e, a screw 422e, although, other attachment mechanisms, such as, but not limited to, those described herein may also be utilized. During implantation, fork prongs 432e may be screwed into 450e and 452e, or to the sternum at positions 450e and 452e thereof, thereby firmly fastening intra-thorax/abdomen respiratory device 400e It is understood that intra-thorax/abdomen respiratory device 400e is likewise attached posteriorly to the ribs, vertebra or vertebral column (not shown), utilizing a same or a different attachment mechanism.

The terminology used herein is for the purpose of describing particular embodiments only and is not intended to be limiting. As used herein, the singular forms "a", "an" and "the" are intended to include the plural forms as well, unless the context clearly indicates otherwise. It will be further understood that the terms "comprises" or "comprising," when used in this specification, specify the presence of stated features, integers, steps, operations, elements, or components, but do not preclude or rule out the presence or addition of one or more other features, integers, steps, operations, elements, components, or groups thereof.

While a number of exemplary aspects and embodiments have been discussed above, those of skill in the art will recognize certain modifications, additions and sub-combinations thereof. It is therefore intended that the following appended claims and claims hereafter introduced be interpreted to include all such modifications, additions and sub-combinations as are within their true spirit and scope.

The invention claimed is:

1. An intra-thorax/abdomen respiratory apparatus comprising an expandable/contractible element; wherein at least part of said expandable/contractible element is configured to be anchored, posteriorly and anteriorly, to a subject's chest bones; and wherein the expandable/contractible element is adapted to cause repeated inhalation and exhalation of air in the subject.

2. The intra-thorax/abdomen respiratory apparatus of claim 1, wherein said subject suffers from respiratory failure.

3. The intra-thorax/abdomen respiratory apparatus of claim 2, being a ventilator.

4. The intra-thorax/abdomen respiratory apparatus of claim 2, further comprising a motor configured to activate the expandable/contractible element, thereby causing inhalation and exhalation of air.

5. The intra-thorax/abdomen respiratory apparatus of claim 1, wherein said expandable/contractible element comprises a rod.

6. The intra-thorax/abdomen respiratory apparatus of claim 1, wherein said expandable/contractible element comprises a material configured to change its configuration in response to an electrical, magnetic and/or mechanical stimulus.

7. The intra-thorax/abdomen respiratory apparatus of claim 1, further comprising a processor, said processor configured to control an operation mode of said intra-thorax/abdomen respiratory apparatus, wherein said operation mode is selected from sleep mode, awake mode, active mode, talk mode, cough mode, weaning mode or any combination thereof.

8. The intra-thorax/abdomen respiratory apparatus of claim 7, wherein said processor is functionally connected to a sensor selected from a pH sensor, a C02 sensor, a capnograph, a PPG sensor or any combination thereof.

9. The intra-thorax/abdomen respiratory apparatus of claim 1, wherein said subject is an autonomously breathing subject.

10. The intra-thorax/abdomen respiratory apparatus of claim 9, wherein breathing by said subject causes expansion and contraction of said expandable/con tractible element, and wherein the expansion and contraction of said expandable/contractible element generates electrical power.

11. The intra-thorax/abdomen respiratory apparatus of claim 10, wherein the electrical power generated can serve as power source to an implanted medical device.

12. The intra-thorax/abdomen respiratory apparatus of claim 11, wherein the implanted medical device comprises a pacemaker.

13. The intra-thorax/abdomen respiratory apparatus of claim 1, further comprising a mechanism mechanically coupled to said expandable/contractible element, wherein said mechanism is configured to cause the expansion and/or the contraction of the expandable/contractible element.

14. The intra-thorax/abdomen respiratory of claim 13, wherein said mechanism is activated by a motor.

15. The intra-thorax/abdomen respiratory apparatus of claim 13, wherein expansion and/or contraction of said expandable/contractible element activates said mechanism.

16. The intra-thorax/abdomen respiratory apparatus of claim 15, wherein activation of said mechanism generates electrical power.

17. The intra-thorax/abdomen respiratory apparatus of claim 1, further comprising an attachment mechanism configured to anchor said intra-thorax/abdomen respiratory apparatus, posteriorly and anteriorly, to the subject's chest bones.

18. A method for providing ventilation to a subject suffering from respiratory failure, the method comprising:
   implanting a ventilator within a thorax/abdomen of the subject, such that an expandable/contractible element of the ventilator is attached to the subject's chest bone anteriorly and posteriorly;
   activating a mechanism causing repeated expansion and contraction of the expandable/contractible element thereby inducing expansion and contraction of the subject's pleural cavity, so as to affect inhalation and exhalation of the subject, respectively.

19. A method for providing electrical energy to an implanted medical device comprising:
   implanting a generator within a thorax/abdomen of a subject implanted with a medical device such that an expandable/contractible element of the generator is attached to the subject's chest bone anteriorly and posteriorly; and such that the subject's inhalation and/or exhalation causes expansion and contraction of the expandable/contractible element, respectively;
   providing a mechanism configured to generate electrical power from the expansion and/or contraction of the expandable/contractible element;
   providing the generated electrical power to the implanted medical device.

20. The method of claim 19, wherein the medical device is a pacemaker.

* * * * *